US011284829B2

(12) United States Patent
Tanishima et al.

(10) Patent No.: US 11,284,829 B2
(45) Date of Patent: Mar. 29, 2022

(54) APPARATUS AND METHOD FOR PROCESSING PHYSIOLOGICAL INFORMATION

(71) Applicant: NIHON KOHDEN CORPORATION, Tokyo (JP)

(72) Inventors: Masami Tanishima, Tokorozawa (JP); Tsuneo Takayanagi, Tokorozawa (JP); Takashi Kaiami, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 305 days.

(21) Appl. No.: 16/156,422

(22) Filed: Oct. 10, 2018

(65) Prior Publication Data

US 2019/0110711 A1 Apr. 18, 2019

(30) Foreign Application Priority Data

Oct. 12, 2017 (JP) .............................. JP2017-198572

(51) Int. Cl.
*A61B 5/364* (2021.01)
*A61B 5/352* (2021.01)
(Continued)

(52) U.S. Cl.
CPC .............. *A61B 5/364* (2021.01); *A61B 5/339* (2021.01); *A61B 5/352* (2021.01); *A61B 5/4035* (2013.01)

(58) Field of Classification Search
CPC ..... A61B 5/0468; A61B 5/044; A61B 5/0456; A61B 5/4035; A61B 5/364; A61B 5/339; A61B 5/352

(Continued)

(56) References Cited

U.S. PATENT DOCUMENTS 5,285,793 A * 2/1994 Slovut .................. A61B 5/0468
128/925
7,933,644 B2 * 4/2011 Wong ................. A61B 5/02405
600/509

(Continued)

FOREIGN PATENT DOCUMENTS

EP 3 210 530 A1 8/2017
JP H06-105818 A 4/1994

(Continued)

OTHER PUBLICATIONS

Japanese Patent Application dated Jun. 22, 2021 issued in Japanese Patent Application No. 2017-198572.

*Primary Examiner* — Catherine M Voorhees
(74) *Attorney, Agent, or Firm* — Pearne & Gordon LLP (57) ABSTRACT

A physiological information processing apparatus includes a processor and a memory storing computer-readable instructions. When the computer-readable instructions are executed by the processor, the apparatus obtains physiological information data indicative of physiological information of a subject, obtains RR interval data including a plurality of RR intervals based on the physiological information data, identifies an RR interval indicative of arrhythmia, and displays the RR interval data as plotted points on a two-dimensional coordinate system having one axis representing an n-th RR interval and another axis representing an (n+1)-th RR interval. The RR interval data is displayed on the two-dimensional coordinate system such that a visual mode of a plurality of first plotted points associated with the RR interval indicative of arrhythmia and a visual mode of plotted points of the RR interval data other than the plurality of first plotted points are different from each other.

17 Claims, 9 Drawing Sheets

(51) Int. Cl.
*A61B 5/00* (2006.01)
*A61B 5/339* (2021.01)

(58) Field of Classification Search
USPC .......................................................... 600/516
See application file for complete search history.

(56) References Cited

U.S. PATENT DOCUMENTS

| | | | |
|---|---|---|---|
| 8,437,841 B2 | 5/2013 | Nanba et al. | |
| 10,244,958 B2* | 4/2019 | Ushiroda | A61B 5/0456 |
| 10,251,576 B2* | 4/2019 | Bardy | A61B 5/044 |
| 2001/0008954 A1* | 7/2001 | Levitan | A61B 5/0245 |
| | | | 600/515 |
| 2005/0010117 A1* | 1/2005 | Agutter | A61B 5/00 |
| | | | 600/484 |
| 2007/0219455 A1* | 9/2007 | Wong | A61B 5/02405 |
| | | | 600/515 |
| 2010/0228139 A1 | 9/2010 | Nanba et al. | |
| 2017/0143225 A1* | 5/2017 | Ushiroda | A61B 5/0456 |
| 2018/0206752 A1* | 7/2018 | Bardy | A61B 5/044 |
| 2019/0076039 A1* | 3/2019 | Young | A61B 5/044 |
| 2019/0110711 A1* | 4/2019 | Tanishima | A61B 5/0468 |
| 2019/0231210 A1* | 8/2019 | Bardy | A61B 5/0205 |

FOREIGN PATENT DOCUMENTS

| | | |
|---|---|---|
| JP | 2003-093360 A | 4/2003 |
| JP | 2004-523250 A | 8/2004 |
| JP | 2010-051387 A | 3/2010 |
| JP | 2010-207347 A | 9/2010 |
| JP | 2010-234000 A | 10/2010 |
| KR | 2004-0095755 A | 11/2004 |

* cited by examiner

APPARATUS AND METHOD FOR PROCESSING PHYSIOLOGICAL INFORMATION

CROSS-REFERENCE TO RELATED APPLICATION

The present application claims priority from Japanese Patent Application No. 2017-198572 filed on Oct. 12, 2017, the entire content of which is incorporated herein by reference.

BACKGROUND

The presently disclosed subject matter relates to a physiological information processing apparatus and a physiological information processing method, and a computer-readable storage medium storing a program which causes a computer to execute the physiological information processing method.

According to a related art method, abnormality of an autonomic nerve function of a patient is identified by using a plurality of RR intervals, each being an interval between adjacent heartbeat waveforms. For example, a related art electrocardiogram analysis apparatus is configured to perform spectrum analysis (frequency analysis) on RR interval data including a plurality of RR intervals and to display the result of the spectrum analysis on a display screen (see, e.g., JPH6-105818A). This allows a medical personnel to see if there is an abnormality of the patient's autonomic nerve function by visually confirming the spectrum analysis result.

In order for a medical personnel to accurately check whether there is an abnormality of the autonomic nerve function of the patient by visually confirming the spectrum analysis result, it is preferable that no RR interval indicative of arrhythmia be included in the RR interval data to be spectrum-analyzed. When an RR interval indicative of arrhythmia is included in the RR interval data, the spectrum of the RR interval data may not accurately reflect the autonomic nerve function of the patient. The RR interval indicative of arrhythmia may be automatically identified and removed from the RR interval data before performing the spectrum analysis on RR interval data. However, because the analysis apparatus is appropriately executing the automatic processing to identify arrhythmia cannot be visually confirmed, a medical personnel may feel anxious about the reliability of the automatic processing executed by the analysis apparatus. From the above viewpoint, there is room to improve usability of the analysis apparatus.

SUMMARY

One or more illustrative aspects of the presently disclosed subject matter provide a physiological information processing apparatus, a physiological information processing method, and a computer-readable storage medium storing a program to cause a computer to execute the physiological information processing method, with improved usability.

According to an aspect of the presently disclosed subject matter, a physiological information processing apparatus includes a processor and a memory storing computer-readable instructions. When the computer-readable instructions are executed by the processor, the processor causes the physiological information processing apparatus to obtain physiological information data indicative of physiological information of a subject, obtain RR interval data including a plurality of RR intervals based on the physiological information data, identify an RR interval indicative of arrhythmia in the RR interval data, and display the RR interval data as a plurality of plotted points on a two-dimensional coordinate system. One axis of the two-dimensional coordinate system represents an n-th RR interval, and another axis of the two-dimensional coordinate system represents an (n+1)-th RR interval. The RR interval data is displayed on the two-dimensional coordinate system such that a visual mode of a plurality of first plotted points associated with the RR interval indicative of arrhythmia and a visual mode of plotted points of the RR interval data other than the plurality of first plotted points are different from each other.

According to another aspect of the presently disclosed subject matter, a physiological information processing apparatus includes a processor and a memory storing computer-readable instructions. When the computer-readable instructions are executed by the processor, the processor causes the physiological information processing apparatus to obtain physiological information data indicative of physiological information of a subject, obtain RR interval data including a plurality of RR intervals based on the physiological information data, identify an RR interval indicative of arrhythmia in the RR interval data, display the RR interval data as a plurality of plotted points on a two-dimensional coordinate system, wherein one axis of the two-dimensional coordinate system represents an n-th RR interval, n being a natural number, and another axis of the two-dimensional coordinate system represents an (n+1)-th RR interval, obtain at least one first parameter associated with an autonomic nerve function of the subject based on the RR interval data other than the RR interval indicative of arrhythmia, and display a first trend graph showing temporal change in the first parameter.

According to another aspect of the presently disclosed subject matter, a physiological information processing apparatus includes a processor and a memory storing computer-readable instructions. When the computer-readable instructions are executed by the processor, the processor causes the physiological information processing apparatus to obtain physiological information data indicative of physiological information of a subject, obtain RR interval data including a plurality of RR intervals based on the physiological information data, displays the RR interval data as a plurality of plotted points on a two-dimensional coordinate system, wherein one axis of the two-dimensional coordinate system represents an n-th RR interval, n is a natural number, and another axis of the two-dimensional coordinate system represents an (n+1)-th RR interval, identify a plurality of first plotted points among a plurality of plotted points of the RR interval data in accordance with an input operation from a user, and obtain at least one first parameter associated with an autonomic nerve function of the subject based on the RR interval associated with the identified first plotted points.

According to another aspect of the presently disclosed subject matter, a physiological information processing method to be executed by a computer is provided. The physiological information processing method includes steps of (a) obtaining physiological information data indicative of physiological information of a subject, (b) obtaining RR interval data including a plurality of RR intervals based on the physiological information data, (c) identifying an RR interval indicative of arrhythmia in the RR interval data, and (d) displaying the RR interval data as a plurality of plotted points on a two-dimensional coordinate system, wherein one axis of the two-dimensional coordinate system represents an n-th RR interval, n being a natural number and another axis of the two-dimensional coordinate system represents an (n+1)-th RR interval. The step (d) includes displaying the RR interval data on the two-dimensional coordinate system such that a visual mode of a plurality of first plotted points associated with the RR interval indicative of arrhythmia and a visual mode of plotted points of the RR interval data other than the plurality of first plotted points are different from each other.

According to another aspect of the presently disclosed subject matter, a physiological information processing method to be executed by a computer is provided. The physiological information processing method includes steps of (a) obtaining physiological information data indicative of physiological information of a subject, (b) obtaining RR interval data including a plurality of RR intervals based on the physiological information data, (c) identifying an RR interval indicative of arrhythmia in the RR interval data, (d) displaying the RR interval data as a plurality of plotted points on a two-dimensional coordinate system, wherein one axis of the two-dimensional coordinate system represents an n-th RR interval, n being a natural number, and another axis of the two-dimensional coordinate system represents an (n+1)-th RR interval, (e) obtaining at least one first parameter associated with an autonomic nerve function of the subject based on the RR interval data other than the RR interval indicative of arrhythmia, and (f) displaying a first trend graph showing temporal change in the first parameter.

According to another aspect of the presently disclosed subject matter, a physiological information processing method to be executed by a computer is provided. The physiological information processing method includes steps of (a) obtaining physiological information data indicative of physiological information of a subject, (b) obtaining RR interval data including a plurality of RR intervals based on the physiological information data, (c) displaying the RR interval data as a plurality of plotted points on a two-dimensional coordinate system, where one axis of the two-dimensional coordinate system represents an n-th RR interval, n being a natural number, and another axis of the two-dimensional coordinate system represents an (n+1)-th RR interval, (d) identifying a plurality of first plotted points among the plurality of plotted points of the RR interval data in accordance with an input operation from a user, and (e) obtaining at least one first parameter associated with an autonomic nerve function of the subject based on the RR interval data associated with the identified first plotted points.

According to another aspect of the presently disclosed subject matter, a computer-readable storage medium is provided. The computer-readable storage medium stores a program which causes a computer to execute at least one of the physiological information processing methods described above.

DETAILED DESCRIPTION

Hereinafter, embodiments of the presently disclosed subject matter will be described with reference to the drawings.

Figure 1:
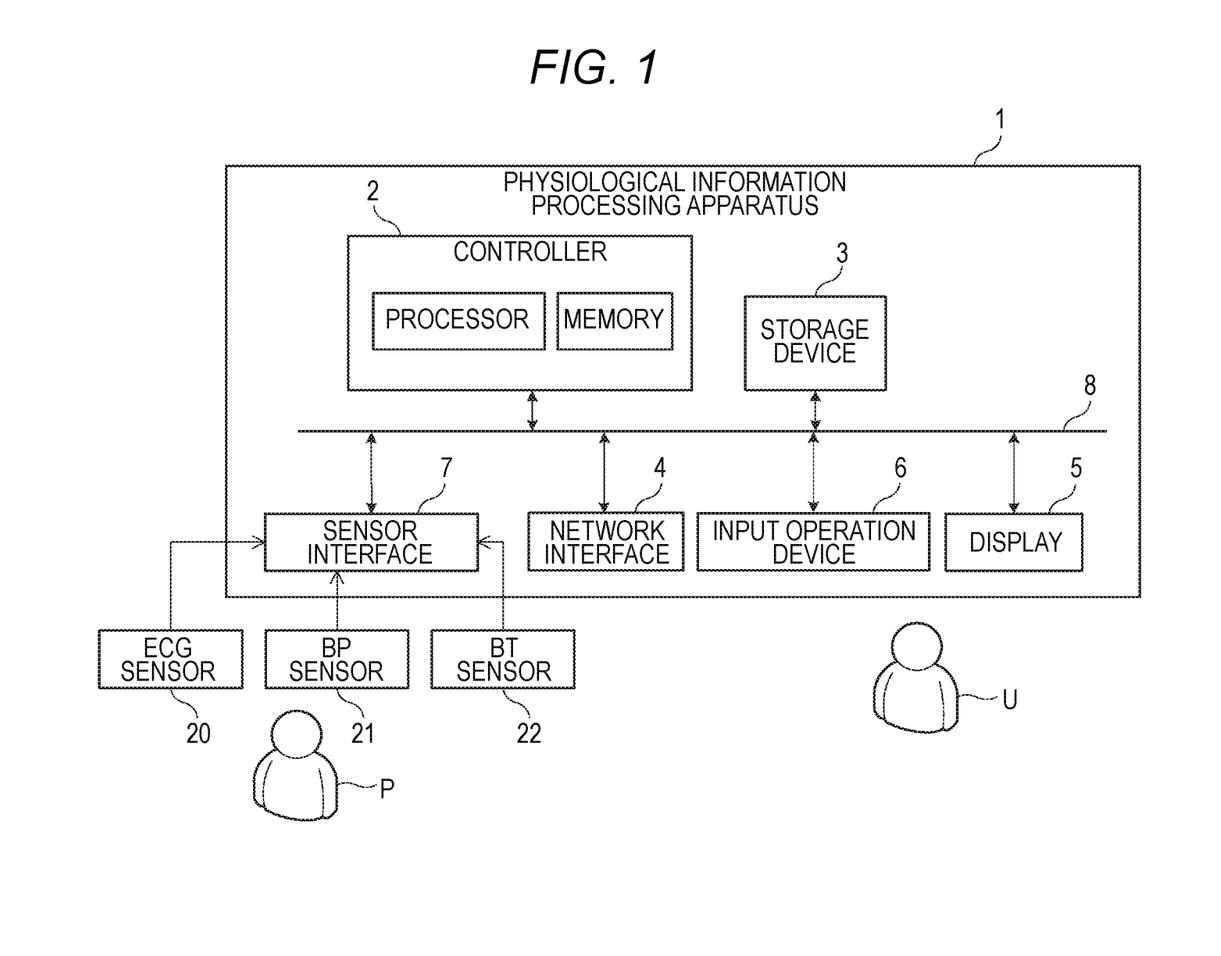
FIG. 1 is a diagram illustrating a hardware configuration of a physiological information processing apparatus according to an embodiment of the presently disclosed subject matter.

FIG. 1 illustrates a hardware configuration of a physiological information processing apparatus 1 according to an embodiment of the presently disclosed subject matter. As illustrated in FIG. 1, the physiological information processing apparatus 1 includes a controller 2, a storage device 3, a network interface 4, a display 5, an input operation device 6 and a sensor interface 7. These are communicably connected to each other through a bus 8.

The processing apparatus 1 may be a patient monitor or the like specifically designed to display a trend graph of a vital sign of a patient P (an example of a subject). Other examples of the processing apparatus 1 include a personal computer, a workstation, a smartphone, a tablet, a wearable device (e.g., a smartwatch or an AR glasses) attachable to a body (e.g., an arm or a head) of a user U (e.g., a medical personnel).

The controller 2 includes at least one memory and at least one processor. The at least one memory is configured to store computer-readable instructions (programs). For example, the at least one memory may include a read only memory (ROM) storing various programs, a RAM random access memory (RAM) having a plurality of work areas storing various programs to be executed by a processor, and/or a flash memory. The at least one processor may include a central processing unit (CPU), a micro processing unit (MPU) and/or a graphics processing unit (GPU). The CPU may include a plurality of CPU cores. The GPU may include a plurality of GPU cores. The at least one processor may be configured to load a designated program stored in the storage device 3 or in the ROM to the RAM, and to execute various processings in cooperation with the RAM.

In particular, the controller 2 may control various operations of the processing apparatus 1 by the processor loading a physiological information processing program to the RAM and executing the program in cooperation with the RAM. Details of the physiological information processing program will be described later.

The storage device 3 may include, for example, a hard disk drive HDD), a solid state drive (SSD), and/or a flash memory, and is configured to store programs and various sets of data. The physiological information processing program may be stored in the storage device 3. Physiological information data (electrocardiogram data, blood pressure data, body temperature data, SpO2 (arterial blood oxygen saturation) data, CO2 data, respiration data, etc.) indicative of physiological information of a patient P may be saved in the storage device 3. For example, the electrocardiogram data obtained by an electrocardiogram sensor 20 may be saved in the storage device 3 through the sensor interface 7.

The network interface 4 is configured to connect the processing apparatus 1 to a communication network. Specifically, the network interface 4 may include various wired connection terminals to communicate with an external apparatus such as a server through the communication network. The network interface 4 may include various processing circuits, an antenna and the like to wirelessly communicate with an external apparatus. The standard for the wireless communication between the external apparatus and the processing apparatus 1 may be Wi-Fi (trademark), Bluetooth (trademark), ZigBee (trademark) or LPWA. The communication network may be a local area network (LAN), a wide area network (WAN), the Internet or the like. For example, the physiological information processing program and the physiological information data may be obtained through the network interface 4 from a server on the communication network.

Figure 3:
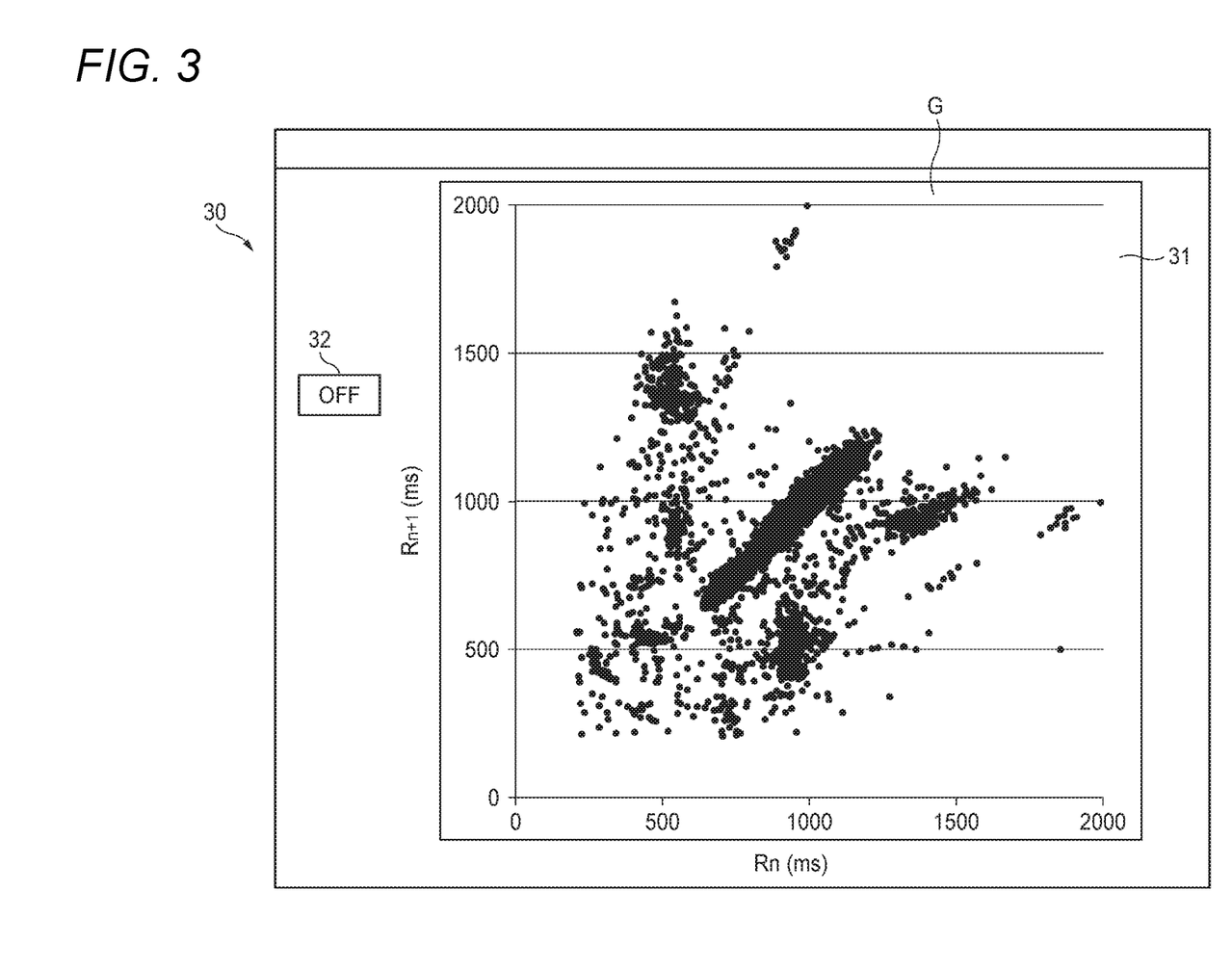
FIG. 3 is a view illustrating an example of a display screen where a two-dimensional coordinate system before an input operation from a user is displayed.

The display 5 may be a liquid crystal display or an organic EL display, or may be a transmissive or a nontransmissive head mounted display attachable to a user's head. Alternatively, the display 5 may be a projector that projects an image onto a screen. For example, a display screen 30 illustrated in FIG. 3 is displayed on the display 5. The display screen 30 is a user interface screen such as a GUI screen. The processing apparatus 1 may not have the display 5. For example, the display screen 30 may be displayed on a display of an external apparatus communicably connected to the processing apparatus 1. In this case, the processing apparatus 1 may display the display screen 30 on the display of the external apparatus.

The input operation device 6 is configured to accept an input operation by a user U (e.g., a medical personnel) operating the processing apparatus 1 and to generate an instruction signal corresponding to the input operation. The input operation device 6 may be, for example, a touch panel superposed on the display 5, an operation button provided on a housing, a mouse and/or a keyboard. The instruction signal generated by the input operation device 6 is sent to the controller 2 through the bus 8, and the controller 2 executes a predetermined operation in response to the instruction signal.

The sensor interface 7 is configured to connect vital sensors such as the electrocardiogram sensor 20, a blood pressure sensor 21 and a body temperature sensor 22 to the processing apparatus 1. The sensor interface 7 may include an input terminal configured to receive physiological information data output from the sensors. The sensor interface 7 may include various processing circuits, an antenna and the like to wirelessly communicate with the sensors. The electrocardiogram sensor 20 is configured to obtain electrocardiogram data of a patient P. The electrocardiogram data is indicative of electrocardiographic waveform of the patient P. The blood pressure sensor 21 is configured to obtain blood pressure data of the patient P. The blood pressure data is indicative of temporal change in the blood pressure of the patient P. The body temperature sensor 22 is configured to obtain the body temperature data of the patient P. The body temperature data is indicative of temporal change in the body temperature of the patient P. The electrocardiogram data, the blood pressure data and the body temperature data are examples of physiological information data indicative of physiological information of the patient P. In the illustrated example, the electrocardiogram data, the blood pressure data and the body temperature data are obtained as examples of the physiological information data. Other examples of the physiological information data that may be further obtained include the SpO2 data indicative of temporal change in SpO2, the CO2 data indicative of temporal change in CO2 value (e.g., CO2 concentration or CO2 discharge amount) and respiration data indicative of temporal change in a respiratory level of the patient.

First Embodiment

Figure 2:
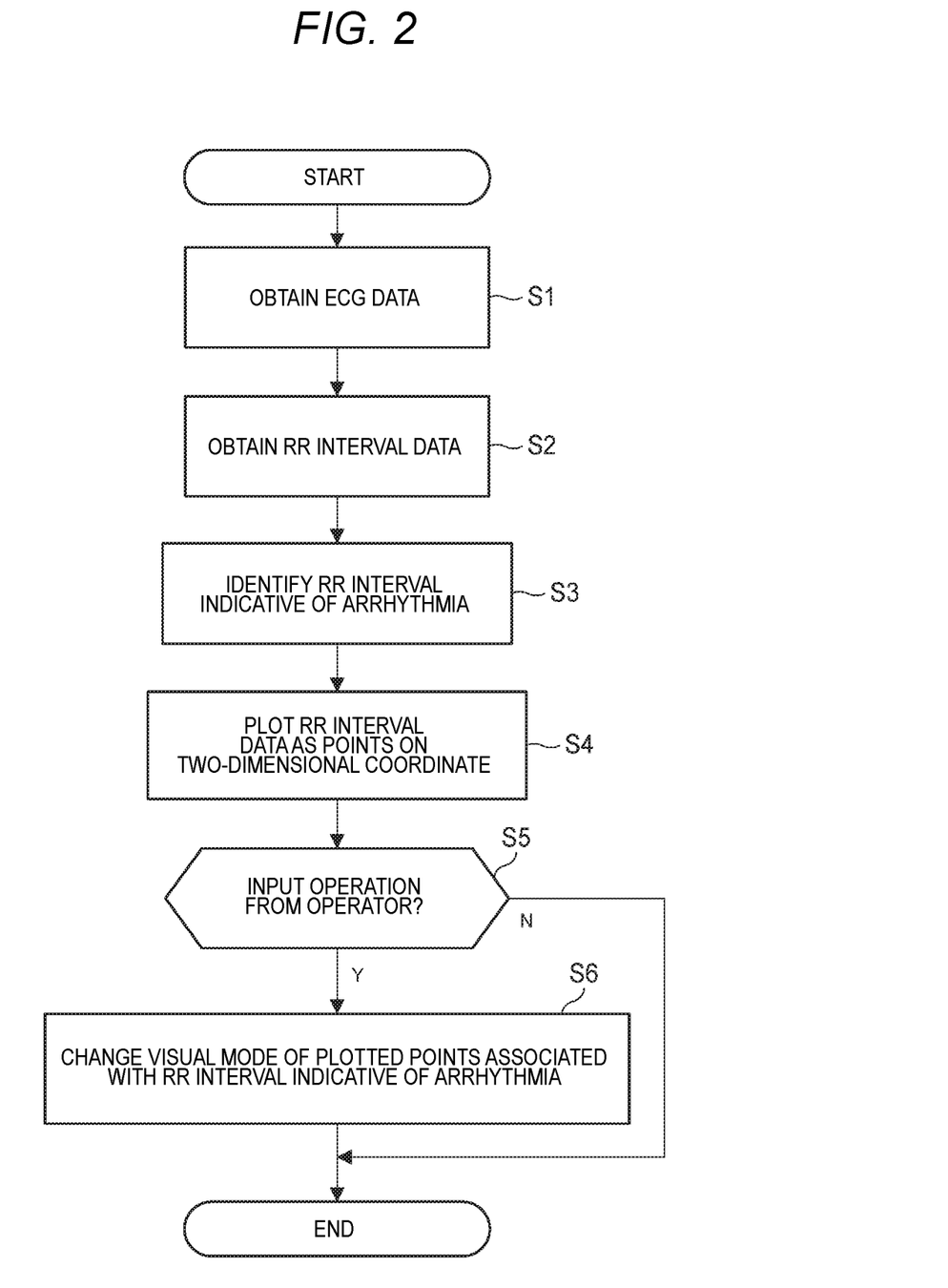
FIG. 2 is a flowchart illustrating an example of a physiological information processing method according to a first embodiment of the presently disclosed subject matter.
Figure 4:
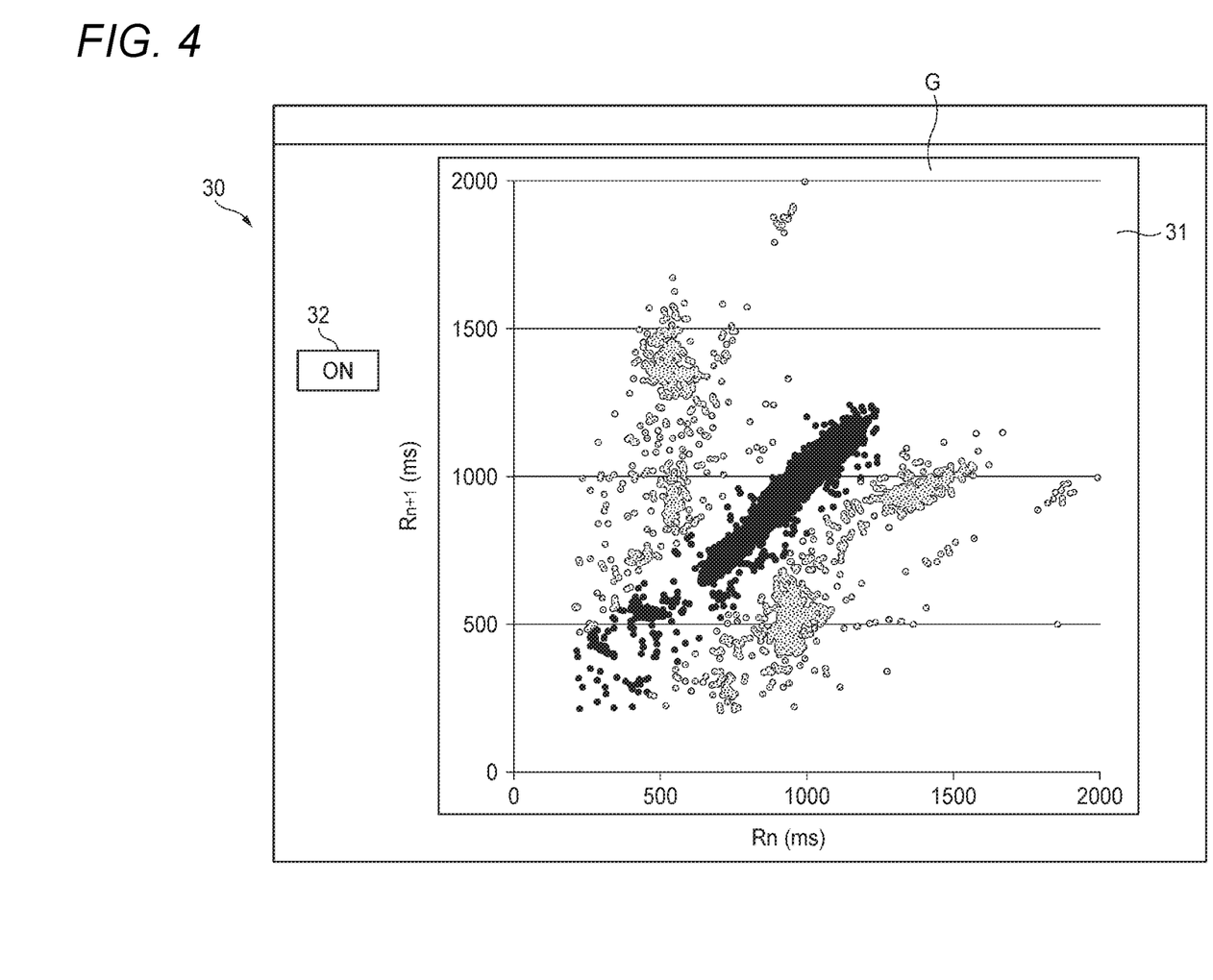
FIG. 4 is a view illustrating an example of the display screen where the two-dimensional coordinate system after an input operation from the user is displayed.

Next, a physiological information processing method according to a first embodiment of the presently disclosed subject matter will be described by referring to FIGS. 2 to 4. FIG. 2 is a flowchart illustrating an example of the physiological information processing method according to the first embodiment. FIG. 3 is a view illustrating an example of the display screen 30 (GUI screen) where a two-dimensional coordinate system G before an input operation from the user U is displayed. FIG. 4 is a view illustrating an example of the display screen 30 after an input operation from the user U.

As illustrated in FIG. 2, at step S1, the controller 2 obtains the electrocardiogram data of the patient P. In particular, the controller 2 may obtain the electrocardiogram data in real time from the electrocardiogram sensor 20, or may obtain the electrocardiogram data stored in the storage device 3. Further, the controller 2 may obtain the electrocardiogram data of the patient P through a server or the like disposed on the communication network. While the controller 2 obtain the electrocardiogram data (an example of the physiological information data) in order to obtain the RR interval data in the first embodiment, instead of the electrocardiogram data, the pulse wave data or the blood pressure data may be obtained in order to obtain the RR interval data. In this case, a pulse wave sensor configured to obtain the pulse wave data of the patient P may be communicably connected to the sensor interface 7 instead of or in addition to the electrocardiogram sensor 20.

Then, the controller 2 obtains the RR interval data based on the electrocardiogram data (step S2). For example, the controller 2 may identify a plurality of RR intervals by identifying the times of the peak points of a plurality of R waves from the electrocardiogram data. The RR interval data may include a plurality of heart rates n and a plurality of RR intervals Rn each associated with one of the plurality of heart rates n (n is a natural number). The RR interval is the interval between the R wave of a heartbeat waveform (QRS waveform) and the R wave of the adjacent heartbeat waveform. For example, the n-th RR interval Rn is defined by the interval between the R wave of the n-th occurring heartbeat waveform Wn and the R wave of the (n+1)-th heartbeat waveform Wn+1.

Then, the controller 2 identifies the RR interval of the RR interval data indicative of arrhythmia (step S3). For example, the controller 2 may identify the RR interval Rn associated with the arrhythmia waveform after identifying the heartbeat waveform Wn (arrhythmia waveform) indicative of arrhythmia based on the shape and size of the heartbeat waveform (QRS waveform) included in the electrocardiogram data. Here, the RR interval Rn associated with the arrhythmia waveform is the interval between the R wave of the arrhythmia waveform and the R wave of the heartbeat waveform adjacent to this arrhythmia waveform.

The controller 2 may identify the RR interval Rn associated with the arrhythmia waveform after identifying the heartbeat waveform Wn (arrhythmia waveform) indicative of arrhythmia based on the parameters other than the RR interval associated with the heartbeat waveform. As described above, at step S3, the RR interval indicative of arrhythmia is automatically identified by the processing apparatus 1.

The controller 2 may identify the n-th RR interval Rn as the RR interval indicative of arrhythmia when coordinates Pn−1(Rn−1, Rn) and coordinates Pn(Rn, Rn+1) do not satisfy the following conditional expression (1):

$$Rn+\alpha \leq Rn+1 \leq Rn-\alpha \tag{1}$$

Here, Rn−1 is the (n−1)-th RR interval. Rn is the n-th RR interval. Rn+1 is the (n+1)-th RR interval. In the above conditional expression (1), a is a given value. For example, a may be set to 100 ms.

Then, at step S4, the controller 2 displays, as a plurality of plotted points, the RR interval data having a plurality of RR intervals Rn (n is a natural number) on the two-dimensional coordinate system G on the display screen 30 (see FIG. 3). As illustrated in FIG. 3, the display screen 30 (GUI screen) has a display area 31 where the two-dimensional coordinate system G is displayed and a command button 32 that accepts an input operation from the user U. The lateral axis of the two-dimensional coordinate system G represents the n-th RR interval Rn, whereas the longitudinal axis of the two-dimensional coordinate system G represents the (n+1)-th RR interval Rn+1. The lateral axis of the two-dimensional coordinate system G may represent the RR interval Rn+1, whereas the longitudinal axis of the two-dimensional coordinate system G may represent the RR interval Rn.

As illustrated in FIG. 3, the RR interval data is displayed as a Lorenz plot (Poincare plot) on the two-dimensional coordinate system G. On the two-dimensional coordinate system G, plotted points are displayed on the coordinates Pn(Rn, Rn+1) formed of the RR intervals Rn and Rn+1. For example, when R10=500 ms and R11=530 ms, a plotted point is displayed on P10(500, 530). In FIG. 3, the display colors of all the plotted points displayed on the two-dimensional coordinate system G are the same color.

Then, at step S5 of FIG. 2, the controller 2 determines whether there is an input operation from the user U. In particular, the controller 2 determines whether there is an input operation by the user U on the command button 32 (see FIG. 3). For example, when the user U specifies the command button 32 (see FIG. 3) through a click operation using a mouse or a touch operation using a finger, the controller 2 determines that there is an input operation by the user U on the command button 32 ("Y" at step S5).

When the determination result at step S5 is "Y", the controller 2 executes the step S6. On the other hand, when the determination result at step S5 is "N", the controller 2 ends the present processing.

At step S6, the controller 2 changes the visual mode (e.g., the display color, display configuration) of a plurality of plotted points associated with the RR interval Rn indicative of arrhythmia (hereinafter, arrhythmia plotted points) of the plurality of plotted points of the RR interval data. In particular, the controller 2 displays the RR interval data on the two-dimensional coordinate system G so that the visual mode of the arrhythmia plotted points and the visual mode of the plotted points of the RR interval data other than the arrhythmia plotted points are different from each other. The arrhythmia plotted points are plotted points displayed on the coordinates Pn(Rn, Rn+1) or plotted points displayed on the coordinates Pn−1(Rn−1, Rn) formed of the RR interval Rn indicative of arrhythmia.

For example, As illustrated in FIG. 4, the controller 2 may change the display color of the arrhythmia plotted points so that the display color of the arrhythmia plotted points is different from the display color of the plotted points other than the arrhythmia plotted points. Moreover, the controller 2 may change the display configuration of the arrhythmia plotted points so that the display configuration of the arrhythmia plotted points is different from the display configuration of the plotted points other than the arrhythmia plotted points. For example, the display configuration of the arrhythmia plotted points may be changed from circular to rectangular. Further, the controller 2 may make the arrhythmia plotted points transparent (non-visible) so that only the plotted points other than the arrhythmia plotted points are visualized.

As described above, according to the first embodiment, the RR interval data is displayed as a Lorenz plot on the two-dimensional coordinate system G so that the visual mode of the arrhythmia plotted points and the visual mode of the plotted points other than the arrhythmia plotted points are different. As described above, by visually confirming a plurality of plotted points visualized on the two-dimensional coordinate system G, the user U (e.g., a medical personnel) can visually recognize the RR interval Rn identified as arrhythmia by the processing apparatus 1 and can intuitively understand whether the processing apparatus 1 is appropriately executing the automatic processing to identify arrhythmia. Consequently, the processing apparatus 1 with improved usability can be provided.

While the visual mode of the arrhythmia plotted points is changed in the first embodiment, the visual mode of the plotted points other than the arrhythmia plotted points may be changed. Further, while the visual mode of the plotted points associated with the RR interval indicative of arrhythmia is changed in accordance with an input operation from the user U in the first embodiment, the visual mode of the plotted points associated with the RR interval indicative of arrhythmia or the visual mode of the plotted points other than the arrhythmia plotted points may be changed without an input operation from the user U.

Figure 5:
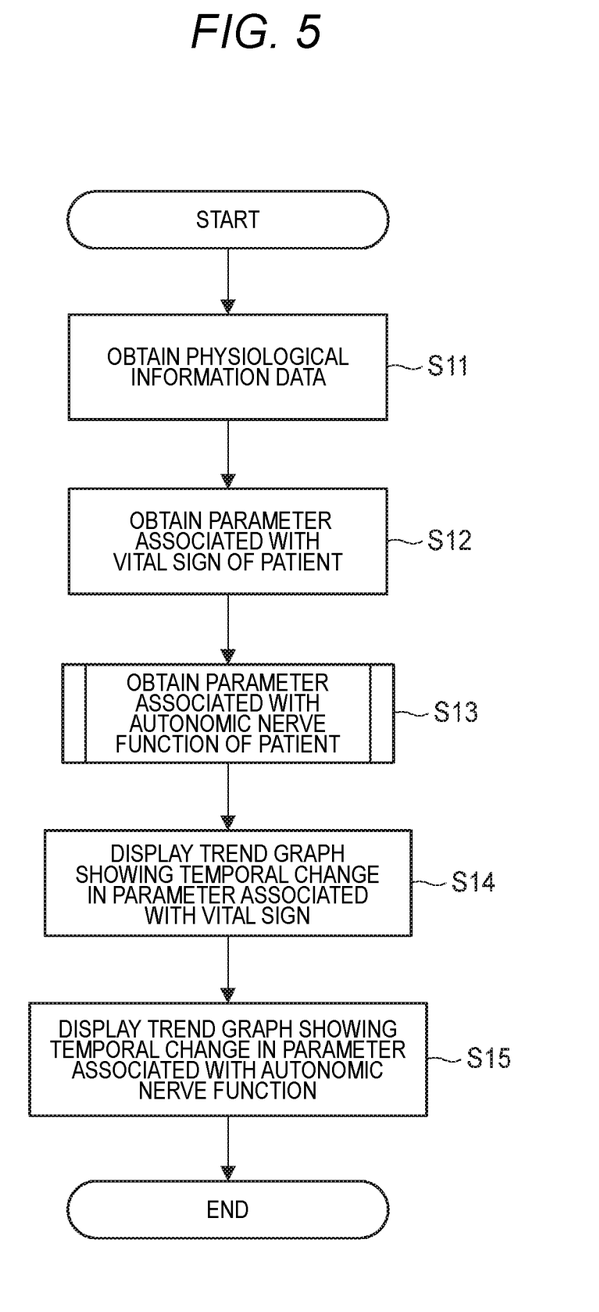
FIG. 5 is a flowchart illustrating an example of the processing of displaying a trend graph of a vital sign and a trend graph of the autonomic nerve function on the display screen.
Figure 6:
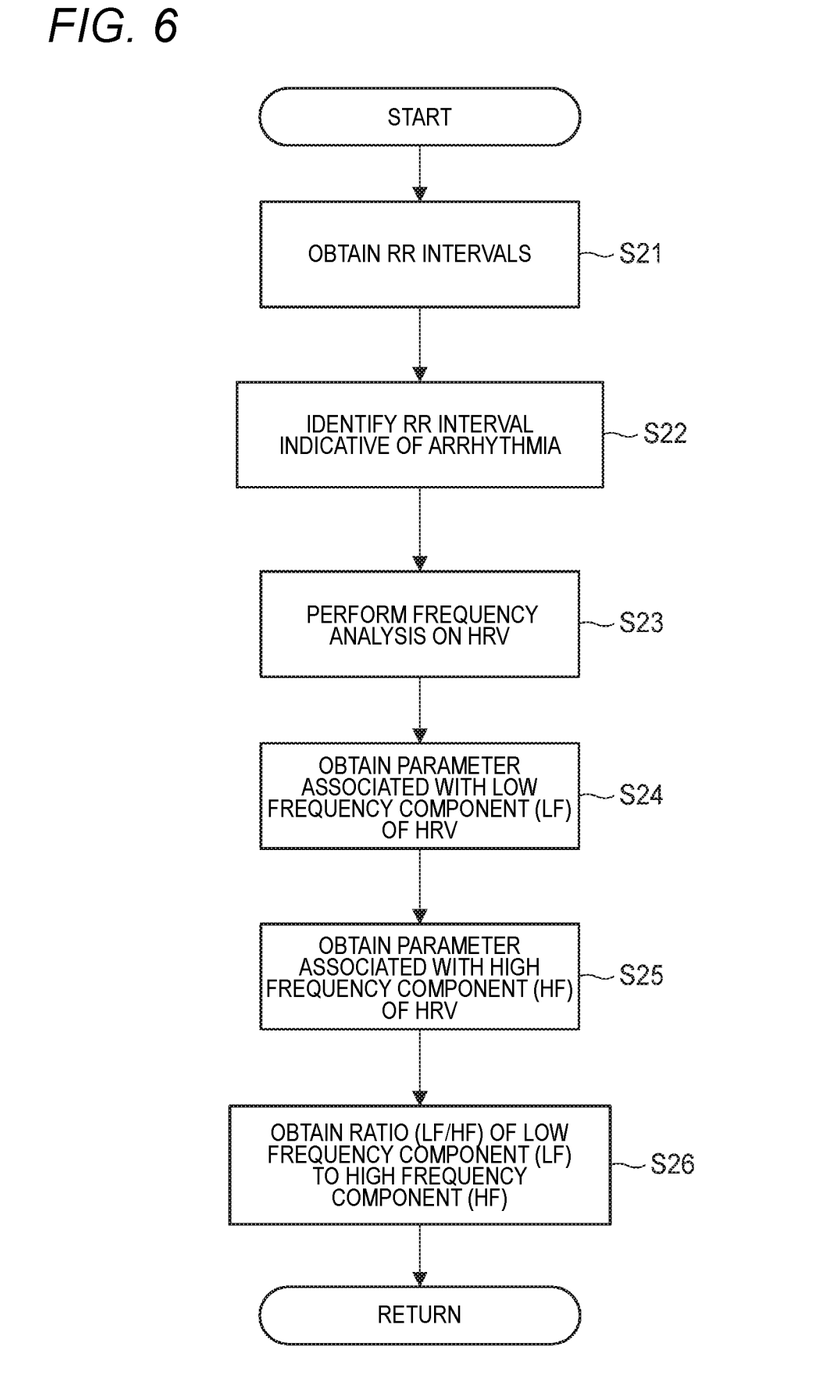
FIG. 6 is a flowchart illustrating an example of the processing of obtaining a parameter associated with the autonomic nerve function of a patient.
Figure 7:
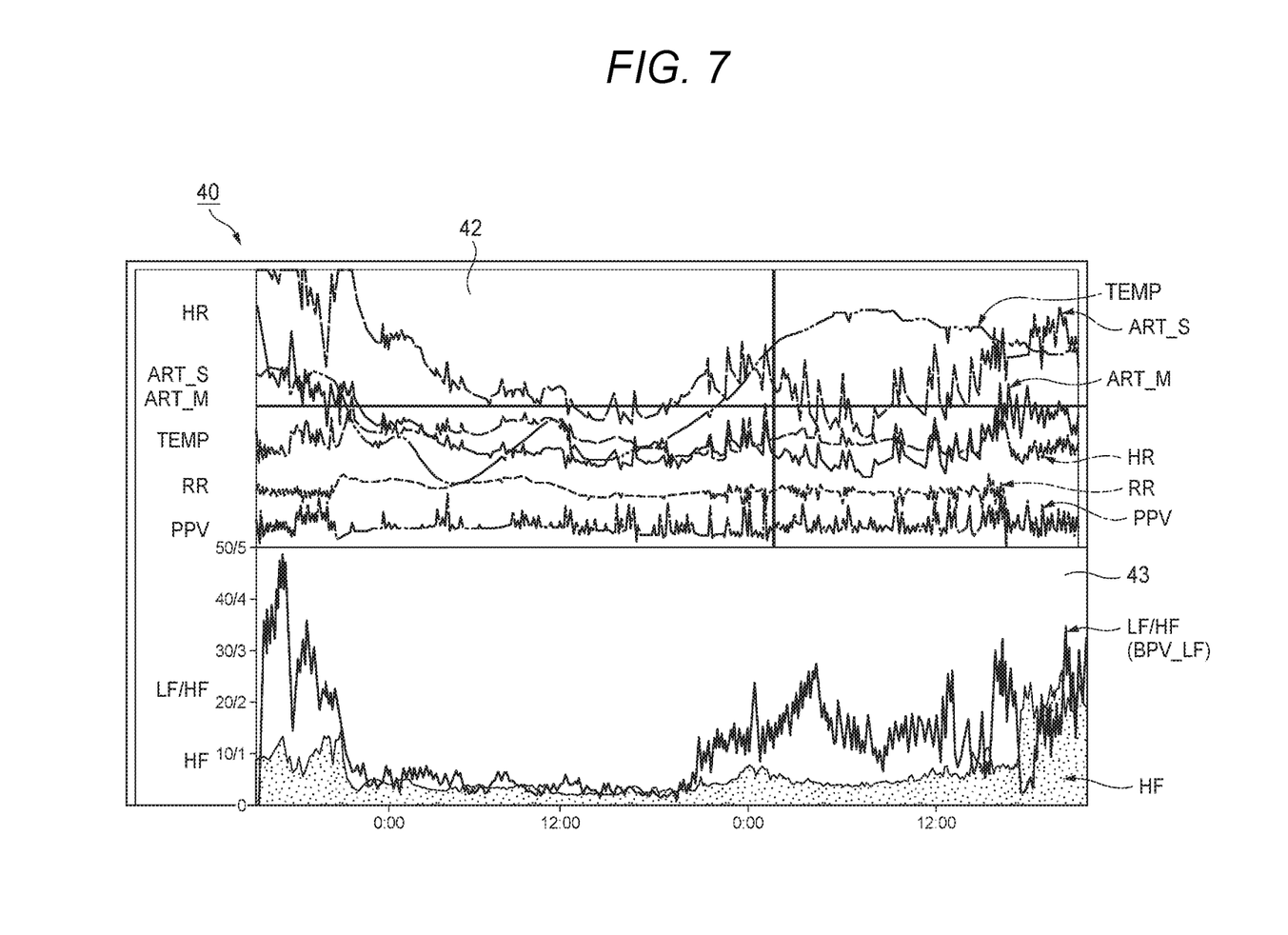
FIG. 7 is a view illustrating an example of the display screen where trend graphs of vital signs and trend graphs of the autonomic nerve function are displayed.

Next, referring to FIGS. 5 to 7, the processing of displaying, on a display screen 40 (see FIG. 7), trend graphs of vital signs of the patient P and trend graphs of the autonomic nerve function of the patient P will be described below. FIG. 5 is a flowchart illustrating an example of the processing of displaying a trend graph of a vital sign and a trend graph of the autonomic nerve function on the display screen 40. FIG. 6 is a flowchart illustrating an example of the processing of obtaining a parameter associated with the autonomic nerve function of the patient P. FIG. 7 is a view illustrating an example of the display screen 40 (GUI screen) where trend graphs of vital signs and trend graphs of the autonomic nerve function are displayed.

As illustrated in FIG. 5, at step S11, the controller 2 obtains the blood pressure data, the electrocardiogram data and the body temperature data as physiological information data. Specifically, when the physiological information data is obtained in real time, the controller 2 may obtain the electrocardiogram data from the electrocardiogram sensor 20 in real time, obtain the blood pressure data from the blood pressure sensor 21 in real time and obtain the body temperature data from the body temperature sensor 22 in real time. On the other hand, the controller 2 may obtain the physiological information data such as the electrocardiogram data stored in the storage device 3. Further, the controller 2 may obtain the physiological information data through a server or the like disposed on the communication network. It may be only the electrocardiogram data that the controller 2 obtains. Moreover, since the RR interval data can also be obtained from the pulse wave data as described above, the pulse wave data may be obtained instead of the electrocardiograph data. Further, the controller 2 may obtain the $SpO_2$ data, the $CO_2$ data and/or the respiration data as the physiological information data.

Then, at step S12, the controller 2 obtains a parameter (an example of the second parameter) associated with a vital sign of the patient P based on the physiological information data (e.g., the electrocardiogram data, the blood pressure data, the body temperature data). In particular, the controller 2 may obtain data indicative of temporal change in the parameter associated with a vital sign of the patient P based on the physiological information data. As illustrated in FIG. 7, the parameter associated with the vital sign is, for example, the heart rate (HR), the body temperature (TEMP), the pulse pressure variability (PPV), the average blood pressure value (ART_M), the maximum blood pressure value (ART_S) and/or the RR interval (RR). Moreover, as the parameter associated with the vital sign, the $SpO_2$ value, the $CO_2$ value and/or the respiratory level may be obtained. When the physiological information data is obtained in real time, the controller 2 may execute the step S12 after obtaining the physiological information data during a predetermined period.

Then, at step S13, the controller 2 obtains a parameter (an example of the first parameter) associated with the autonomic nerve function of the patient P based on the physiological information data (e.g., the electrocardiogram data, the blood pressure data). In particular, the controller 2 may obtain data indicative of temporal change in the parameter associated with the autonomic nerve function of the patient P based on the physiological information data. Referring to FIG. 6, the processing of obtaining the parameter associated with the autonomic nerve function of the patient P will be described below.

As illustrated in FIG. 6, at step S21, the controller 2 obtains a plurality of RR intervals Rn (n is a natural number) based on the electrocardiogram data. Then, the controller 2 identifies the RR interval, indicative of arrhythmia, of the RR interval data including the plurality of RR intervals Rn (step S22). The step S22 corresponds to the step S3 illustrated in FIG. 2. Here, the RR interval data may include a plurality of RR intervals Rn (n is a natural number) each associated with one of the plurality of heart rates n. Moreover, the RR interval data may include a plurality of RR intervals associated with one time with which each is associated.

Then, the controller 2 performs frequency analysis on the heat rate variability (HRV) of the patient P (step S23). Specifically, the controller 2 performs frequency analysis (e.g., the fast Fourier transformation (FFT)) on the RR interval data indicative of temporal fluctuation in the plurality of RR intervals.

Then, the controller 2 obtains a parameter associated with the low frequency component (LF) of the heart rate variability (HRV) (step S24). For example, the controller 2 may identify the peak intensity of the power spectrum of the RR interval data in a low frequency band (e.g., 0.05 Hz to 0.15 Hz) or the integral value of the intensity as the parameter associated with the low frequency component (LF) of the heat rate variability (hereinafter, LF parameter). The controller 2 may obtain the LF parameter at a time t1 (or a time t2) by performing frequency analysis on the RR interval data between the times t1 and t2 (t1<t2).

Then, the controller 2 obtains a parameter associated with the high frequency component (HF) of the heart rate variability (HRV) (step S25). For example, the controller 2 may identify the peak intensity of the power spectrum of the RR interval data in a high frequency band (e.g., 0.15 Hz to 0.40 Hz) or the integral value of the intensity as the parameter associated with the high frequency component (HF) of the heat rate variability (hereinafter, HF parameter). The controller 2 may obtain the HF parameter at the time t2 (or a time t3) by performing frequency analysis on the RR interval data between the times t2 to t3 (t2<t3). The HF parameter is a parameter associated with the parasympathetic nerve function of the patient P. For example, the medical personnel can determine that the parasympathetic nerve function of the patient P has deteriorated when the value of the HF parameter is lower than a predetermined threshold value during a predetermined period.

Then, the controller 2 obtains the ratio (LF/HF) of the low frequency component (LF) of the heart rate variability to the high frequency component (HF) of the heat rate variability (step S26). Specifically, the controller 2 obtains the ratio of the LF parameter to the HF parameter as an LF/HF parameter. The LF/HF parameter is a parameter associated with the sympathetic nerve function of the patient P. For example, the medical personnel can determine that the sympathetic nerve function of the patient P has deteriorated when the value of the LF/HF parameter is lower than a predetermined threshold value during a predetermined period.

As described above, the controller 2 can obtain the parameters associated with the autonomic nerve function of the patient P from the electrocardiogram data. In particular, the controller 2 can obtain the HF parameter indicative of the parasympathetic nerve function of the patient P and the LF/HF parameter indicative of the sympathetic nerve function of the patient P from the electrocardiogram data.

The controller 2 may obtain a parameter associated with the autonomic nerve function of the patient P from the blood pressure data. In this case, the controller 2 performs frequency analysis on the maximum blood pressure variability (BPV) of the patient P after obtaining the blood pressure data. Specifically, the controller 2 performs frequency analysis (e.g., FFT) on the maximum blood pressure data after obtaining the maximum blood pressure data indicative of temporal change in the maximum blood pressure of the patient P. Thereafter, the controller 2 obtains a parameter associated with the low frequency component (LF) of the maximum blood pressure variability (BPV). For example, the controller 2 identifies the peak intensity of the power spectrum of the maximum blood pressure data in the low frequency band or the integral value of the intensity as the parameter associated with the low frequency component (LF) of the BPV (hereinafter, BPV_LF parameter). The BPV_LF parameter is a parameter associated with the sympathetic nerve function of the patient P. For example, the medical personnel can determine that the sympathetic nerve function of the patient P has deteriorated when the value of the BPV_LF parameter is lower than a predetermined threshold value during a predetermined period.

Returning to FIG. 5, at step S14, the controller 2 displays, in a display area 42 of the display screen 40, a trend graph (an example of the second trend graph) showing temporal change in a parameter (e.g., the heart rate (HR)) associated with a vital sign of the patient P (see FIG. 7). As illustrated in FIG. 7, trend graphs of the heart rate, the body temperature, the pulse pressure variability, the average blood pressure value, the maximum blood pressure value and the RR interval may be displayed in the display area 42.

Then, at step S15, the controller 2 displays, in a display area 43 of the display screen 40, a trend graph (an example of the first trend graph) indicative of temporal change in a parameter associated with the autonomic nerve function of the patient P. As illustrated in FIG. 7, the controller 2 may display, in the display area 43, a trend graph of the HF parameter associated with the parasympathetic nerve function of the patient P and a trend graph of the LF/HF parameter associated with the sympathetic nerve function of the patient P.

A trend graph of the BPV_LF parameter instead of the LF/HF parameter may be displayed in the display area 43 as the trend graph of the parameter associated with the sympathetic nerve function. In this case, display switching between the trend graph of the LF/HF parameter and the trend graph of the BPV_LF parameter may be made in accordance with an input operation by the user U.

As illustrated in FIG. 7, the display area 42 and the display area 43 may be displayed next to each other such that the time axis of the display area 42 and the time axis of the display area 43 are synchronized with each other. In other words, the time axis of the trend graph of the vital sign displayed in the display area 42 and the time axis of the trend graph of the autonomic nerve function displayed in the display area 43 may coincide with each other (that is, these two trend graphs may share a single time axis.). As described above, the user U (e.g., a medical personnel) can more accurately and quickly check the disease condition of the patient by visually confirming the temporal change in the vital sign and the autonomic nerve function of the patient P displayed on the display screen 40. In particular, the user U can see changes of the disease condition of the patient P, the risk of occurrence of arrhythmia and the like. As described above, the processing apparatus 1 with improved usability can be provided.

Since at least one parameter associated with the autonomic nerve function of the patient P is obtained based on the RR interval data other than the RR interval indicative of arrhythmia, the reliability of the parameter can be improved.

When the physiological information data (e.g., the electrocardiogram data, the blood pressure data, the body temperature data, the SpO2 data, the CO2 data, the respiration data) is obtained from the sensors in real time, at steps S14 and S15, the controller 2 may update the trend graph (an example of the second trend graph) of the vital sign and the trend graph (an example of the first trend graph) of the autonomic nerve function according to the lapse of time. In this case, the series of processing illustrated in FIG. 5 may be repetitively executed at predetermined intervals. The value of the trend graph shown at the right end of the display screen 40 is the newest value, whereas the value of the trend graph shown at the left end of the display screen 40 is the oldest value.

As described above, when the trend graph of the vital sign and the trend graph of the autonomic nerve function are updated according to the lapse of time, the medical personnel can check the disease condition of the patient in real time by visually confirming these trend graphs updated in real time on the display screen 40. Thus, the usability of the processing apparatus 1 can be further improved.

The display screen 30 illustrated in FIG. 3 and the display screen 40 illustrated in FIG. 7 may be simultaneously displayed on the display 5. A trend graph of a vital sign and/or a trend graph of the autonomic nerve function may be displayed on the display screen 30 illustrated in FIG. 3. In particular, the two-dimensional coordinate system G where the RR interval data is displayed as a plurality of plotted points and a trend graph of the autonomic nerve function may be displayed in line with each other on the same screen. In this case, the user U can visually recognize whether the RR interval data includes the RR interval indicative of arrhythmia and can confirm abnormality of the autonomic nerve function of the patient P and the disease condition of the patient P based on the abnormality by visually confirming the RR interval data displayed as a Lorenz plot on the two-dimensional coordinate system G and the trend graph of the autonomic nerve function.

Second Embodiment

Figure 8:
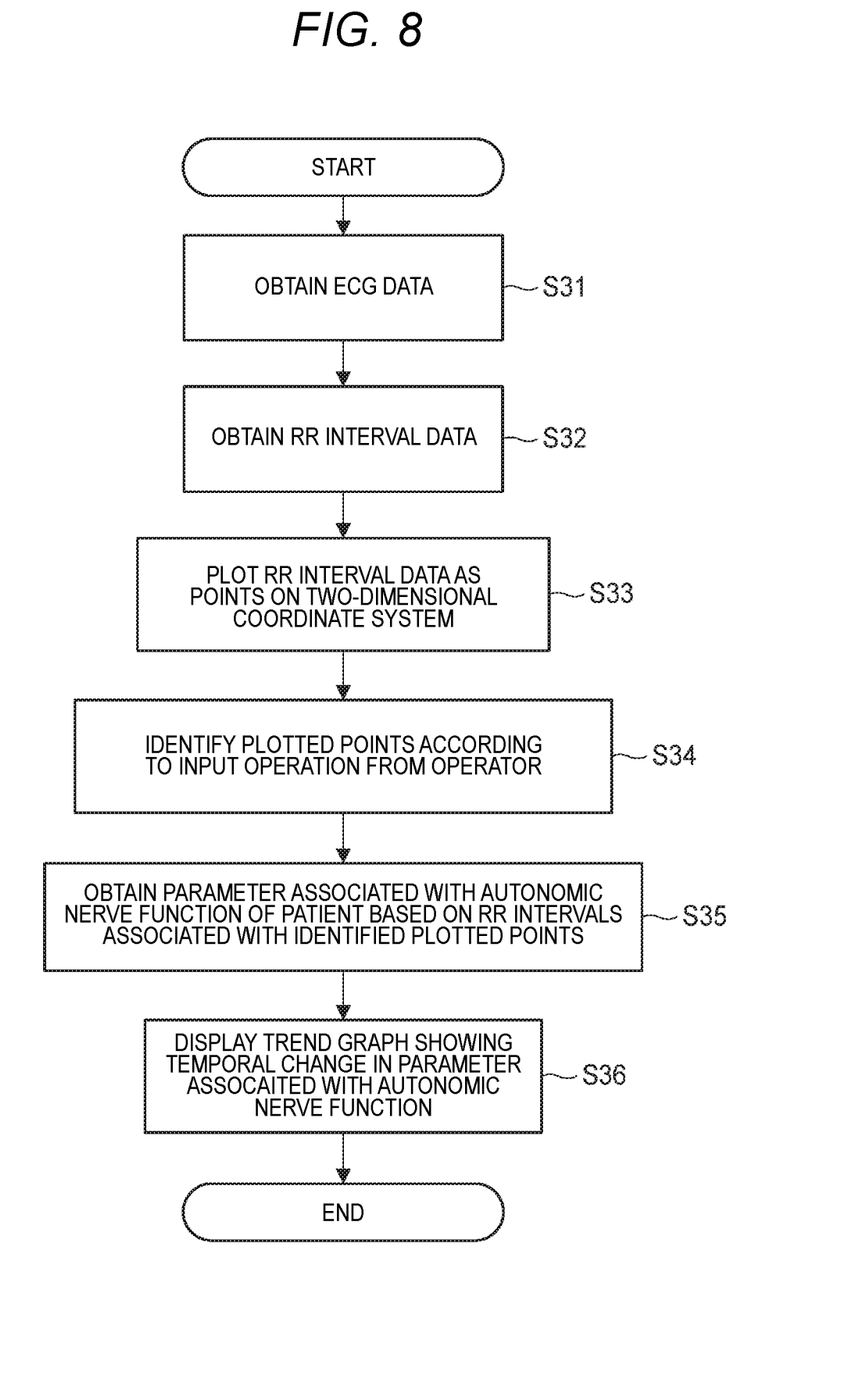
FIG. 8 is a flowchart illustrating an example of the physiological information processing method according to a second embodiment of the presently disclosed subject matter.
Figure 9:
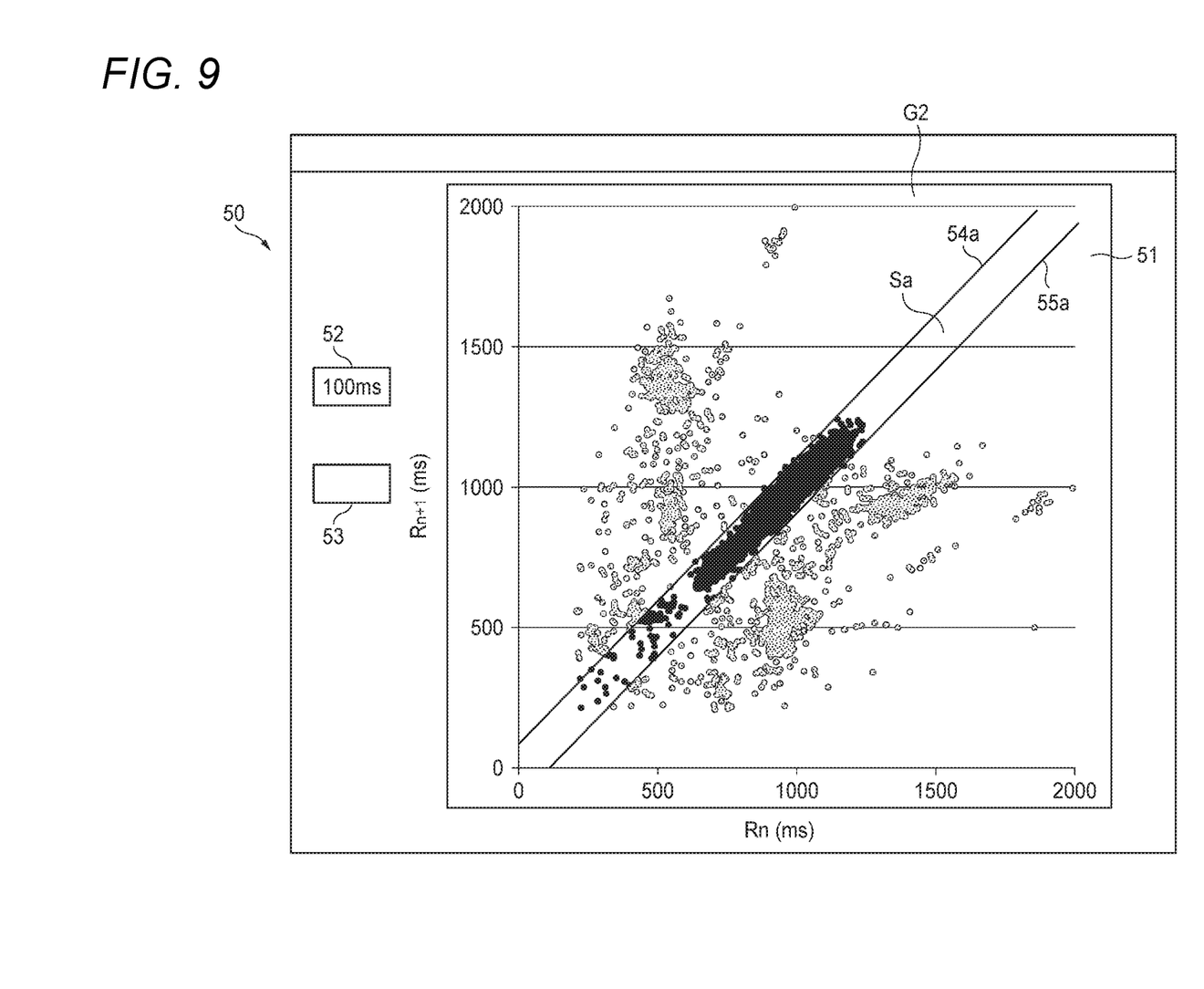
FIG. 9 is a view illustrating a manner where a plurality of plotted points of RR interval data displayed on the two-dimensional coordinate system are selected by the user.

Next, a physiological information processing method according to a second embodiment of the presently disclosed subject matter will be described below by referring to FIGS. 8 and 9. FIG. 8 is a flowchart illustrating an example of the physiological information processing method according to the second embodiment. FIG. 9 is a view illustrating a manner where a plurality of plotted points of the RR interval data displayed on the two-dimensional coordinate system G are selected by the user U.

As illustrated in FIG. 8, at step S31, the controller 2 obtains the electrocardiogram data of the patient P. Then, the controller 2 obtains the RR interval data including a plurality of RR intervals Rn (n is a natural number) based on the electrocardiogram data (step S32). The processings of steps S31 and S32 correspond to the processings of steps S1 and S2 illustrated in FIG. 2, respectively.

Then, at step S33, the controller 2 displays, as a plurality of plotted points, the RR interval data on a two-dimensional coordinate system G2 on a display screen 50 (see FIG. 9). As illustrated in FIG. 9, the display screen 50 (GUI screen) has a display area 51 where the two-dimensional coordinate system G2 is displayed, a display area 52 indicating the value of a (described later) and a command button 53 that accepts an input operation from the user U. The lateral axis of the two-dimensional coordinate system G2 represents the n-th RR interval Rn, whereas the longitudinal axis of the two-dimensional coordinate system G2 represents the (n+1)-th RR interval Rn+1. The lateral axis of the two-dimensional coordinate system G2 may represent the RR interval Rn+1, whereas the longitudinal axis of the two-dimensional coordinate system G2 may represent the RR interval Rn.

As illustrated in FIG. 9, the RR interval data is displayed as a Lorenz plot (Poincare plot) on the two-dimensional coordinate system G2. On the two-dimensional coordinate system G2, plotted points are displayed on the coordinates Pn(Rn, Rn+1) formed of RR intervals Rn and Rn+1.

Then, at step S34, the controller 2 identifies a plurality of plotted points among the plurality of plotted points of the RR interval data in accordance with an input operation from the user U. As illustrated in FIG. 9, the user U can identify a plurality of plotted points by moving two plotted point identifying lines 54a and 55a. Here, the plotted point identifying line 54a represents a straight line of Rn+1=Rn+α, whereas the plotted point identifying line 55a represents a straight line of Rn+1=Rn−α (α is a given value). For example, when the value of a is 100 ms, "100 ms" may be displayed in the display area 52. The plurality of plotted points are identified by the two plotted point identifying lines 54a and 55a. That is, the plurality of plotted points existing within an area Sa defined by the two plotted point identifying lines 54a and 55a are identified by the user U.

The coordinates Pn(Rn, Rn+1) of the plurality of plotted points existing within the area Sa satisfy the following conditional expression (2):

$$Rn+\alpha \leq Rn+1 \leq Rn-\alpha \quad (2)$$

As described later, the RR intervals Rn and Rn+1 associated with the coordinates Pn(Rn, Rn+1) of the plurality of plotted points existing within the area Sa and selected by the user U are used for calculating a parameter associated with the autonomic nerve function.

In the initial state (before an input operation by the user U is executed), $\alpha$ may be set to $\alpha 1$. In this case, the plotted point identifying line 54a may represent a straight line of Rn+1=Rn+$\alpha 1$, whereas the plotted point identifying line 55a may represent a straight line of Rn+1=Rn−$\alpha 1$. Further, the coordinates Pn(Rn, Rn+1) of the plotted points existing within the area Sa in the initial state may satisfy the following conditional expression (3):

$$Rn+\alpha 1 \leq Rn+1 \leq Rn-\alpha 1 \quad (3)$$

The user U may move the two plotted point identifying lines 54a and 55a by dragging and dropping at least one of the two plotted point identifying lines 54a and 55a by using a mouse. Moreover, when the input operation device 6 includes a touch panel that accepts an input operation from the user U, the user U may move the two plotted point identifying lines 54a and 55a by performing a touch operation on at least one of the two plotted point identifying lines 54a and 55. For example, when the plotted point identifying line 54a is moved by an input operation by the user U, the plotted point identifying line 55a may move automatically. Since the plotted point identifying lines 54a and 55a can be moved by an input operation by the user U as described above, the area Sa can be made variable. Consequently, a plurality of plotted points can be selected by an input operation by the user U.

The area Sa may be determined by the user directly inputting the value of a. For example, an input area where the value of $\alpha$ can be input may be provided within the display screen 50.

The controller 2 may change the visual mode (e.g., the display color, the display configuration) of the plotted points existing within the area Sa or the visual mode of the plotted points existing outside the area Sa so that the visual mode of the plotted points existing within the area Sa and the visual mode of the plotted points existing outside the area Sa are different. In this regard, the visual mode of the plotted points existing within the area Sa or the visual mode of the plotted points existing outside the area Sa may be changed by the user U performing a click operation or a touch operation on the command button 53.

For example, As illustrated in FIG. 9, the controller 2 may change the display color of the plotted points existing within the area Sa so that the display color of the plotted points existing within the area Sa is different from the display color of the plotted points existing outside the area Sa. In this regard, the controller 2 may make the plotted points existing within the area Sa or the plotted points existing outside the area Sa transparent (non-visible). Moreover, the controller 2 may change the display configuration of the plotted points existing within the area Sa or the display configuration of the plotted points existing outside the area Sa so that the display configuration of the plotted points existing within the area Sa is different from the display configuration of the plotted points existing outside the area Sa.

Then, at step S35, the controller 2 obtains the parameter (an example of the first parameter) associated with the autonomic nerve function of the patient P (e.g., the sympathetic nerve function, the parasympathetic nerve function) based on the RR intervals Rn and Rn+1 associated with a plurality of plotted points identified by the user U (i.e., existing within the area Sa). For example, the controller 2 obtains the parameter associated with the autonomic nerve function of the patient P by performing frequency analysis (FFT, etc.) on the RR interval data formed of the identified RR intervals Rn and Rn+1 after identifying the RR intervals Rn and Rn+1 of the coordinates Pn(Rn, Rn+1) of the plurality of plotted points existing within the area Sa. Specifically, when P3(R3, R4) exists within the area Sa, the RR intervals R3 and R4 are used for the calculation of the parameter indicative of the autonomic nerve function of the patient P. The processing of calculating the parameter associated with the autonomic nerve function corresponds to the processings of steps S23 to S26 illustrated in FIG. 6. For example, the controller 2 may obtain the HF parameter associated with the parasympathetic nerve function of the patient P and the LF/HF parameter associated with the sympathetic nerve function of the patient P.

Then, at step S36, the controller 2 displays a trend graph (an example of the trend graph of the autonomic nerve function) indicative of temporal change in the parameter associated with the autonomic nerve function of the patient P. The step S36 corresponds to the step S15 illustrated in FIG. 5. For example, the controller 2 may display the trend graph of the autonomic nerve function and the trend graph of the vital sign in the display areas 43 and 42 of the display screen 40, respectively.

As described above, according to the present embodiment, a plurality of plotted points, existing within the area Sa, of a plurality of plotted points of the RR interval data are identified in accordance with an input operation from the user U (medical personnel). Thereafter, a parameter (e.g., the HF parameter, the LF/HF parameter) associated with the autonomic nerve function of the patient P is obtained based on the RR intervals Rn and Rn+1 associated with the coordinates Pn(Rn, Rn+1) of the identified plurality of plotted points. As described above, the user U can select a plurality of plotted points used for the calculation of the parameter indicative of the autonomic nerve function of the patient P while looking at a plurality of plotted points visualized as a Lorenz plot on the two-dimensional coordinate system G2. Consequently, since the user U can intuitively select the RR interval not indicative of arrhythmia or the like (that is, the RR interval reflecting the autonomic nerve function), the processing apparatus 1 with improved usability can be provided.

Further, the user U can intuitively understand abnormality of the autonomic nerve function of the patient P and/or abnormality of a vital sign of the patient P and change in the disease condition of the patient P by visually confirming a trend graph of the autonomic nerve function and a trend graph of the vital sign displayed on the display screen 40.

In the present embodiment, the RR interval associated with the plotted points existing within the area Sa is used for the calculation of the parameter indicative of the autonomic nerve function of the patient P. On the other hand, the controller 2 may use an RR interval other than the identified RR intervals Rn and Rn+1 for the calculation of the parameter indicative of the autonomic nerve function of the patient P after identifying the RR intervals Rn and Rn+1 associated with the coordinates Pn(Rn, Rn+1) on the plotted points outside the area Sa. In this case, the RR interval indicative of arrhythmia and the RR interval adjacent to the RR interval indicative of arrhythmia are not used for the calculation of the parameter indicative of the autonomic nerve function.

While in the present embodiment, the RR interval associated with the coordinates of the plotted points existing within the area Sa and the RR interval other than the RR interval associated with the coordinates of the plotted points outside the area Sa are used for the calculation of the parameter indicative of the autonomic nerve function of the patient P, the present embodiment is not limited thereto. For example, when the user U directly specifies a plurality of plotted points existing within the area Sa through a drag operation using a finger, the controller 2 may use the RR interval associated with the coordinates of the plotted points directly specified by the user U for the calculation of the parameter indicative of the autonomic nerve function. As described above, the controller 2 may use the RR interval associated with the plotted points directly specified by a drag operation by the user U for the calculation of the parameter indicative of the autonomic nerve function.

Moreover, in the present embodiment, the display screen 50 illustrated in FIG. 9 and the display screen 40 illustrated in FIG. 7 may be simultaneously displayed on the display 5. Moreover, a trend graph of a vital sign and/or a trend graph of the autonomic nerve function may be displayed on the display screen 50 illustrated in FIG. 9. In particular, the two-dimensional coordinate system G2 where the RR interval data is displayed as a plurality of plotted points and a trend graph of the autonomic nerve function may be displayed in line with each other on the same display screen.

To implement the processing apparatus 1 by means of software, a physiological information processing program may be pre-installed in the storage device 3 or a ROM. Alternatively, the physiological information processing program may be stored in a computer-readable storage medium such as a magnetic disk (e.g., an HDD, a floppy disk), an optical disk (e.g., a CD-ROM, a DVD-ROM, Blu-ray (trademark) disc), a magneto-optical disk (e.g., an MO) or a flash memory (e.g., an SD card, a USB memory, or an SSD). In this case, the physiological information processing program stored in the storage medium may be installed in the storage device 3. The processor may load the physiological information processing program stored in the storage device 3 to the RAM and execute the program loaded to the RAM. This is how the physiological information processing method may be executed by the processing apparatus 1.

The physiological information processing program may be downloaded through the network interface 4 from a computer on the communication network. In this case, the downloaded program may be similarly installed in the storage device 3.

While the presently disclosed subject matter has been described with reference to certain embodiments thereof, the scope of the presently disclosed subject matter n is not limited to the embodiments described above, and it will be understood by those skilled in the art that various changes and modifications may be made therein without departing from the scope as defined by the appended claims.

What is claimed is:

1. A physiological information processing apparatus comprising:
a processor;
a display device; and
a memory storing computer-readable instructions,
wherein, when the computer-readable instructions are executed by the processor, the processor causes the physiological information processing apparatus to:
obtain physiological information data indicative of physiological information of a subject,
obtain RR interval data including a plurality of RR intervals based on the physiological information data,
identify an RR interval indicative of arrhythmia in the RR interval data, and
display, on the display device, the RR interval data as a plurality of plotted points on a two-dimensional coordinate system,
wherein one axis of the two-dimensional coordinate system represents an n-th RR interval, n being a natural number, and another axis of the two-dimensional coordinate system represents an (n+1)-th RR interval, and
wherein the RR interval data is displayed on the two-dimensional coordinate system such that a visual mode of a plurality of first plotted points associated with the RR interval indicative of arrhythmia and a visual mode of plotted points of the RR interval data other than the plurality of first plotted points are different from each other.

2. The physiological information processing apparatus according to claim 1, wherein the physiological information processing apparatus is configured to obtain at least one first parameter associated with an autonomic nerve function of the subject based on the RR interval data other than the RR interval indicative of arrhythmia.

3. The physiological information processing apparatus according to claim 2, wherein the physiological information processing apparatus is configured to display a first trend graph showing temporal change in the first parameter.

4. The physiological information processing apparatus according to claim 1, wherein the physiological information processing apparatus is configured to obtain at least one second parameter associated with a vital sign of the subject based on the physiological information data, and to display a second trend graph showing temporal change in the second parameter.

5. A physiological information processing apparatus comprising:
a processor;
a display device; and
a memory storing computer-readable instructions,
wherein, when the computer-readable instructions are executed by the processor, the processor causes the physiological information processing apparatus to:
obtain physiological information data indicative of physiological information of a subject,
obtain RR interval data including a plurality of RR intervals based on the physiological information data,
display, on the display device, the RR interval data as a plurality of plotted points on a two-dimensional coordinate system, wherein one axis of the two-dimensional coordinate system represents an n-th RR interval, n is a natural number, and another axis of the two-dimensional coordinate system represents an (n+1)-th RR interval,
identify a plurality of first plotted points among a plurality of plotted points of the RR interval data in accordance with an input operation from a user, and
obtain at least one first parameter associated with an autonomic nerve function of the subject based on the RR interval associated with the identified first plotted points.

6. The physiological information processing apparatus according to claim 5,
wherein the physiological information processing apparatus is configured to display a first trend graph showing temporal change in the first parameter over a period of time, and
wherein one axis of the graph represents the period of time, and another axis of the graph represents a value of the first parameter.

7. The physiological information processing apparatus according to claim 5, wherein the physiological information processing apparatus is configured to obtain at least one second parameter associated with a vital sign of the subject based on the physiological information data, and to display a second trend graph showing temporal change in the second parameter.

8. The physiological information processing apparatus according to claim 1, wherein the visual mode of the first plotted points associated with the RR interval indicative of arrhythmia and the visual mode of the plotted points of the RR interval data other than the plurality of first plotted points are different in color or shape.

9. The physiological information processing apparatus according to claim 1, wherein the RR interval data is displayed in real time.

10. The physiological information processing apparatus according to claim 6, wherein the RR interval data and the first trend graph are displayed in real time.

11. A physiological information processing method to be executed by a computer, the physiological information processing method comprising steps of:
(a) obtaining physiological information data indicative of physiological information of a subject;
(b) obtaining RR interval data including a plurality of RR intervals based on the physiological information data;
(c) identifying an RR interval indicative of arrhythmia in the RR interval data; and
(d) displaying, on a display device, the RR interval data as a plurality of plotted points on a two-dimensional coordinate system, wherein one axis of the two-dimensional coordinate system represents an n-th RR interval, n being a natural number and another axis of the two-dimensional coordinate system represents an (n+1)-th RR interval,
wherein the step (d) includes displaying the RR interval data on the two-dimensional coordinate system such that a visual mode of a plurality of first plotted points associated with the RR interval indicative of arrhythmia and a visual mode of plotted points of the RR interval data other than the plurality of first plotted points are different from each other.

12. The physiological information processing method according to claim 11, further comprising a step of (e) obtaining at least one first parameter associated with an autonomic nerve function of the subject based on the RR interval data other than the RR interval indicative of arrhythmia.

13. The physiological information processing method according to claim 12, further comprising a step of (f) displaying a first trend graph showing temporal change in the first parameter.

14. The physiological information processing method according to claim 11, further comprising steps of:
(g) obtaining at least one second parameter associated with a vital sign of the subject based on the physiological information data; and
(h) displaying a second trend graph showing temporal change in the second parameter.

15. A computer-readable storage medium storing a program which causes a computer to execute the physiological information processing method according to claim 11.

16. The physiological information processing method according to claim 11, wherein the visual mode of the first plotted points associated with the RR interval indicative of arrhythmia and the visual mode of the plotted points of the RR interval data other than the plurality of first plotted points are different in color or shape.

17. The physiological information processing method according to claim 11, wherein the RR interval data is displayed in real time.

* * * * *